(12) United States Patent
Hong et al.

(10) Patent No.: US 7,115,723 B1
(45) Date of Patent: Oct. 3, 2006

(54) HUMANIZED ANTIBODY SPECIFIC FOR SURFACE ANTIGEN PRE-S1 OF HBV AND PREPARATION METHOD THEREOF

(75) Inventors: Hyo Jeong Hong, Taejon-si (KR); Chun Jeih Ryu, Taejon-si (KR); Hyangsuk Hur, Taejon-si (KR)

(73) Assignees: Korea Institute of Science and Technology, Seoul (KR); Korea Green Cross Corporation, Seoul (KR)

( * ) Notice: Subject to any disclaimer, the term of this patent is extended or adjusted under 35 U.S.C. 154(b) by 0 days.

(21) Appl. No.: 09/856,114

(22) PCT Filed: Nov. 19, 1999

(86) PCT No.: PCT/KR99/00699

§ 371 (c)(1), (2), (4) Date: May 18, 2001

(87) PCT Pub. No.: WO00/31141

PCT Pub. Date: Jun. 2, 2000

(30) Foreign Application Priority Data

Nov. 19, 1998 (KR) .................................. 98-49663

(51) Int. Cl.
*C07H 21/04* (2006.01)

(52) U.S. Cl. ............... 536/23.1; 424/130.1; 424/133.1; 530/387.1; 530/387.3

(58) Field of Classification Search ............... 536/23.1; 424/130.1, 133.1; 530/387.1, 387.3
See application file for complete search history.

(56) References Cited

FOREIGN PATENT DOCUMENTS

WO    WO 93/16192 A1    8/1993

OTHER PUBLICATIONS

C.J. Ryu et al., "A Humanized Antibody with Specificity for Hepatitis B Surface Antigen", *Hum. Antibod. Hybridomas*, vol. 7, No. 3, 1996, pp. 113-122.
C.J. Ryu et al., "In Vitro Neuralization of Hepatitis B Virus by Monoclonal Antibodies Against the Viral Surface Antigen", *Journal of Medical Virology*, vol. 52, 1997, pp. 226-233.
Neurath and Kent, "The pre-S Region of Hepadnavirus Envelope Proteins", *Adv. Virus Res.*, vol. 34, 1998, pp. 65-142.
Iwarson, et al., "Neutralization of Hepatitis B Virus Infectivity by a Murine Monoclonal Antibody: An Experimental Study in the Chimpanzee" *J. Med. Virol.*, vol. 16, 1985, pp. 89-96.
Itoh et al., "A Synthetic Peptide Vaccine Involving the Product of the Pre-S(2) Region of Hepatitis B Virus DNA: Protective Efficacy in Chimpanzees", *Proc. Natl. Acad. Sci.*, USA, vol. 83, 1986, pp. 9174-9178.
Budkowska et al., "Monoclonol Antibody Recognizing Pre-S(2) Epitope of Hepatitis B Virus: Characterization of Pre-S(2) Epitope and Anti-Pre-S(2) Antibody", *J. Med. Virol.*, vol. 20, 1986, pp. 111-125.
Milich et al., "Distinct H-2-linked Regulation of T-cell Responses to the pre-S and S Regions of the Same Hepatitis B Surface Antigen Polypeptide Allows Circumvention of Nonresponsiveness to the S Region", Proc. *Natl. Acad. Sci.*, USA, vol. 82, 1985, pp. 8168-8172.
Milich et al., "Immune Response to the Pre-S(1) Region of the Hepatitis B Surface Antigen (HbsAg): A Pre-S(1)-Specific T Cell Response can Bypass Nonresponsiveness to the Pre-S(2) and S Regions of HBsAg$^{1}$", *J. Immunol*, vol. 137, 1986, pp. 315-322.
Heermann et al., "Large Surface Proteins of Hepatitis B Virus Containing the Pre-s Sequence", *J. Virol*, vol. 52, No. 2, 1984, pp. 396-402.
Neurath et al., "Identification and Chemical Synthesis of a Host Cell Receptor Binding Site on Hepatitis B Virus", *Cell*, vol. 46, 1986, pp. 429-436.
Pontisso et al., "Identification of an Attachment Site for Human Liver Plasma Membranes on Hepatitis B Virus Particles", *Virology*, vol. 173, 1989, pp. 522-530.
Neurath et al., "Antibodies to Synthetic Peptides from the Pre-S1 Region of the Hepatitis B Virus (HBV) Envelope (env) Protein are Virus-neutralizing and Protective", *Vaccine*, vol. 7, 1989, pp. 234-236.

*Primary Examiner*—Jeffrey Stucker
*Assistant Examiner*—Louise Wang
(74) *Attorney, Agent, or Firm*—Gates & Cooper LLP

(57) ABSTRACT

The present invention relates to humanized antibodies specific for HBV surface antigen pre-S1, which show binding affinity similar to mouse monoclonal antibody and which show remarkably reduced immunogenicity since they have less mouse-derived amino acid residues. Thus, the humanized antibodies of the present invention may be useful for the prevention of HBV infection and for the treatment of hepatitis B.

8 Claims, 11 Drawing Sheets

FIG. 1a

|  | | Q | V | Q | L | Q | Q | S | G | P | E | L | V | K | P | |
|---|---|---|---|---|---|---|---|---|---|---|---|---|---|---|---|---|
| KR127VH | | CAG | GTC | CAG | CTG | CAG | CAG | TCT | GGA | CCT | GAA | CTG | GTG | AAG | CCT | 42 |
| DP7 | | CAG | GTG | CAG | CTG | GTG | CAG | TCT | GGG | GCT | GAG | GTG | AAG | AAG | CCT | |
| HZII | | CAG | GTC | CAG | CTG | GTG | CAG | TCT | GGA | GCT | GAA | GTG | AAG | AAG | CCT | |
| HZI | | CAG | GTC | CAG | CTG | GTG | CAG | TCT | GGA | GCT | GAA | GTG | GTG | AAG | CCT | |
| HZIII | | CAG | GTC | CAG | CTG | GTG | CAG | TCT | GGA | GCT | GAA | GTG | AAG | AAG | CCT | 42 |
| HZII | | - | - | - | - | V | - | - | - | A | - | V | K | - | - | |
| HZI | | - | - | - | - | V | - | - | - | A | - | V | - | - | - | |
| HZIII | | - | - | - | - | V | - | - | - | A | - | V | K | - | - | |

|  | | G | A | S | V | K | I | S | C | K | A | S | G | Y | A | |
|---|---|---|---|---|---|---|---|---|---|---|---|---|---|---|---|---|
| KR127VH | | GGG | GCC | TCA | GTG | AAG | ATT | TCC | TGC | AAA | GCT | TCT | GGC | TAC | GCA | 84 |
| DP7 | | GGG | GCC | TCA | GTG | AAG | GTT | TCC | TGC | AAG | GCA | TCT | GGA | TAC | ACC | |
| HZII | | GGG | GCC | TCA | GTG | AAG | GTT | TCC | TGC | AAA | GCT | TCT | GGC | TAC | ACC | |
| HZI | | GGG | GCC | TCA | GTG | AAG | GTT | TCC | TGC | AAA | GCT | TCT | GGC | TAC | GCA | |
| HZIII | | GGG | GCC | TCA | GTG | AAG | GTT | TCC | TGC | AAA | GCT | TCT | GGC | TAC | ACC | 84 |
| HZII | | - | - | - | - | - | V | - | - | - | - | - | - | - | T | |
| HZI | | - | - | - | - | - | V | - | - | - | - | - | - | - | - | |
| HZIII | | - | - | - | - | - | V | - | - | - | - | - | - | - | T | |

|  | | F | S | S | S | W | M | N | W | V | K | Q | R | P | G | |
|---|---|---|---|---|---|---|---|---|---|---|---|---|---|---|---|---|
| KR127VH | | TTC | AGT | AGT | TCT | TGG | ATG | AAC | TGG | GTG | AAG | CAG | AGG | CCT | GGA | 126 |
| DP7 | | TTC | ACC | AGC | TAC | TAT | ATG | CAC | TGG | GTG | CGA | CAG | GCC | CCT | GGA | |
| HZII | | TTC | ACC | AGT | TAC | TGG | ATG | AAC | TGG | GTG | CGA | CAG | GCC | CCT | GGA | |
| HZI | | TTC | AGT | AGT | TCT | TGG | ATG | AAC | TGG | GTG | CGA | CAG | GCC | CCT | GGA | |
| HZIII | | TTC | ACC | AGT | TCT | TGG | ATG | AAC | TGG | GTG | CGA | CAG | GCC | CCT | GGA | |
| HZII | | - | T | - | Y | - | - | - | - | - | R | - | A | - | - | |
| HZI | | - | - | - | - | - | - | - | - | - | R | - | A | - | - | |
| HZIII | | - | T | - | - | - | - | - | - | - | R | - | A | - | - | |

|  | | Q | G | L | E | W | I | G | R | I | Y | P | G | D | G | |
|---|---|---|---|---|---|---|---|---|---|---|---|---|---|---|---|---|
| KR127VH | | CAG | GGT | CTT | GAG | TGG | ATT | GGA | CGG | ATT | TAT | CCT | GGA | GAT | GGA | 168 |
| DP7 | | CAA | GGG | CTT | GAG | TGG | ATG | GGA | ATA | ATC | AAC | CCT | AGT | GGT | GGT | |
| HZII | | CAG | GGT | CTT | GAG | TGG | ATG | GGA | CGG | ATT | TAT | CCT | GGA | GAT | GGA | |
| HZI | | CAG | GGT | CTT | GAG | TGG | ATT | GGA | CGG | ATT | TAT | CCT | GGA | GAT | GGA | |
| HZIII | | CAG | GGT | CTT | GAG | TGG | ATG | GGA | CGG | ATT | TAT | CCT | GGA | GAT | GGA | |
| HZII | | - | - | - | - | - | M | - | - | - | - | - | - | - | - | |
| HZI | | - | - | - | - | - | - | - | - | - | - | - | - | - | - | |
| HZIII | | - | - | - | - | - | M | - | - | - | - | - | - | - | - | |

|  | | D | T | N | Y | N | G | K | F | K | G | K | A | T | L | |
|---|---|---|---|---|---|---|---|---|---|---|---|---|---|---|---|---|
| KR127VH | | GAT | ACT | AAC | TAC | AAT | GGG | AAG | TTC | AAG | GGC | AAG | GCC | ACA | CTG | 210 |
| DP7 | | AGC | ACA | AGC | TAC | GCA | CAG | AAG | TTC | CAG | GGC | AGA | GTC | ACC | ATG | |
| HZII | | GAT | ACT | AAC | TAC | GCA | CAG | AAG | TTC | CAG | GGC | AGA | GTC | ACA | ATG | |
| HZI | | GAT | ACT | AAC | TAC | GCA | CAG | AAG | TTC | CAG | GGC | AAG | GCC | ACA | CTG | |
| HZIII | | GAT | ACT | AAC | TAC | GCA | CAG | AAG | TTC | CAG | GGC | AGA | GTC | ACA | ATG | |
| HZII | | - | - | - | - | A | Q | - | - | Q | - | R | V | - | M | |
| HZI | | - | - | - | - | A | Q | - | - | Q | - | - | - | - | - | |
| HZIII | | - | - | - | - | A | Q | - | - | Q | - | R | V | - | M | |

FIG. 1b

```
           T   A   D   K   S   S   S   T   A   Y   M   Q   L   S
KR127VH   ACT GCA GAC AAA TCC TCC AGC ACA GCC TAC ATG CAG CTC AGC 252
DP7       ACC AGG GAC ACG TCC ACG AGC ACA GTC TAC ATG GAG CTG AGC
HZII      ACT GCA GAC ACG TCC ACG AGC ACA GTC TAC ATG GAG CTC AGC
HZI       ACC GCA GAC AAA TCC ACG AGC ACA GCC TAC ATG GAG CTG AGC
HZIII     ACT GCA GAC AAA TCC ACG AGC ACA GTC TAC ATG GAG CTC AGC
HZII       -   -   -   T   -   T   -   -   V   -   -   E   -   -
HZI        -   -   -   -   -   T   -   -   -   -   -   E   -   -
HZIII      -   -   -   -   -   T   -   -   V   -   -   E   -   -

S   L   T   S   V   D   S   A   V   Y   F   C   A   R
KR127VH   AGC CTG ACC TCT GTG GAC TCT GCG GTC TAT TTC TGT GCA AGA 294
DP7       AGC CTG AGA TCT GAG GAC ACG GCC GTG TAT TAC TGT GCG AGA
HZII      AGC CTG AGA TCT GAG GAC ACG GCG GTC TAT TAC TGT GCA AGA
HZI       AGC CTG AGA TCT GAG GAC ACG GCG GTC TAT TTC TGT GCA AGA
HZIII     AGC CTG AGA TCT GAG GAC ACG GCG GTC TAT TAC TGT GCA AGA
HZII       -   -   R   -   E   -   T   -   -   -   Y   -   -   -
HZI        -   -   R   -   E   -   T   -   -   -   -   -   -   -
HZIII      -   -   R   -   E   -   T   -   -   -   Y   -   -   -

E   Y   D   E   A   Y   W   G   Q   G   T   L   V   T
KR127VH   GAG TAC GAC GAG GCT TAC TGG GGC CAA GGG ACT CTG GTC ACT 336
HZII      GAG TAC GAC GAG GAC TAC TGG GGC CAA GGG ACT CTG GTC ACT
HZI       GAG TAC GAC GAG GCT TAC TGG GGC CAA GGG ACT CTG GTC ACT
HZIII     GAG TAC GAC GAG GCT TAC TGG GGC CAA GGG ACT CTG GTC ACT
HZII       -   -   -   -   D   -   -   -   -   -   -   -   -   -
HZI        -   -   -   -   -   -   -   -   -   -   -   -   -   -
HZIII      -   -   -   -   -   -   -   -   -   -   -   -   -   -

V   S   A
KR127VH   GTC TCT GCA 345

HZII      GTC TCT TCA
HZI       GTC TCT TCA
HZIII     GTC TCT TCA
HZII       -   -   S
HZI        -   -   S
HZIII      -   -   S
```

FIG. 3a

```
         D   I   L   M   T   Q   T   P   L   I   L   S   V   T
KR127VK  GAT ATC TTG ATG ACC CAA ACT CCA CTT ATT TTG TCG GTT ACC  42
DPK12    GAT ATT GTG ATG ACC CAG ACT CCA CTC TCT CTG TCC GTC ACC
HZII     GAT ATC GTG ATG ACC CAA ACT CCA CTT TCT TTG TCG GTT ACC
HZII      -   -   V   -   -   -   -   -   -   S   -   -   -   -
HZI       -   -   -   -   -   -   -   -   -   S   -   -   -   -

I   G   Q   P   A   S   I   S   C   K   S   S   Q   S
KR127VK  ATT GGA CAA CCA GCC TCT ATC TCT TGC AAG TCA AGT CAG AGC  84
DPK12    CCT GGA CAG CCG GCC TCC ATC TCC TGC AAG TCT AGT CAG AGC
HZII     CCT GGA CAA CCA GCC TCT ATC TCT TGC AAG TCA AGT CAG AGC
HZII      P   -   -   -   -   -   -   -   -   -   -   -   -   -
HZI       P   -   -   -   -   -   -   -   -   -   -   -   -   -

L   L   Y   S   N   G   K   T   Y   L   N   W   L   L
KR127VK  CTC TTA TAT AGT AAT GGA AAA ACC TAT TTG AAT TGG TTA TTA  126
DPK12    CTC CTG CAT AGT GAT GGA AAG ACC TAT TTG TAT TGG TAC CTG
HZII     CTC TTA TAT AGT AAT GGA AAA ACC TAT TTG AAT TGG TTA TTA
HZII      -   -   -   -   -   -   -   -   -   -   -   -   -   -
HZI       -   -   -   -   -   -   -   -   -   -   -   -   -   -

Q   R   P   G   Q   S   P   K   R   L   I   Y   L   V
KR127VK  CAG AGG CCA GGC CAG TCT CCA AAG CGC CTA ATC TAT CTG GTG  168
DPK12    CAG AAG CCA GGC CAG CCT CCA CAG CTC CTG ATC TAT GAA GTT
HZII     CAG AAG CCA GGC CAG CCT CCA CAG CTC CTA ATC TAT CTG GTG
HZII      -   K   -   -   -   P   -   Q   L   -   -   -   -   -
HZI       -   K   -   -   -   -   -   -   -   -   -   -   -   -

S   K   L   D   S   G   V   P   D   R   F   T   G   S
KR127VK  TCT AAA CTG GAC TCT GGA GTC CCT GAC AGG TTC ACT GGC AGT  210
DPK12    TCC AAC CGG TTC TCT GGA GTG CCA GAT AGG TTC AGT GGC AGC
HZII     TCT AAA CGG TTC TCT GGA GTC CCT GAC AGG TTC AGT GGC AGT
HZII      -   -   R   F   -   -   -   -   -   -   -   S   -   -
HZI       -   -   -   -   -   -   -   -   -   -   -   S   -   -
```

FIG. 3b

```
            G    S    G    T    D    F    T    L    K    I    I    R    V    E
KR127VK    GGA  TCA  GGA  ACA  GAT  TTT  ACA  CTG  AAA  ATC  ATC  AGA  GTG  GAG   252
DPK12      GGG  TCA  GGG  ACA  GAT  TTC  ACA  CTG  AAA  ATC  AGC  CGG  GTG  GAG
HZII       GGA  TCA  GGA  ACA  GAT  TTT  ACA  CTG  AAA  ATC  AGC  AGA  GTG  GAG
HZII        -    -    -    -    -    -    -    -    -    -    S    -    -    -
HZI         -    -    -    -    -    -    -    -    -    -    S    -    -    -

A    E    D    L    G    V    Y    Y    C    V    Q    G    T    H
KR127VK    GCT  GAG  GAT  TTG  GGA  GTT  TAT  TAC  TGC  GTG  CAA  GGT  ACA  CAT   294
DPK12      GCT  GAG  GAT  GTT  GGG  GTT  TAT  TAC  TGC  ATG  CAA  AGT  ATA  CAG
HZII       GCT  GAG  GAT  GTT  GGA  GTT  TAT  TAC  TGC  GTG  CAA  GGT  ACA  CAT
HZII        -    -    -    V    -    -    -    -    -    -    -    -    -    -
HZI         -    -    -    V    -    -    -    -    -    -    '    -    -    -

F    P    Q    T    F    G    G    G    T    K    L    E    I    K
KR127VK    TTT  CCT  CAG  ACG  TTC  GGT  GGA  GGC  ACC  AAG  CTG  GAA  ATC  AAA   336
DPK12      CTT  CCT  CC
HZII       TTT  CCT  CAG  ACG  TTC  GGT  GGA  GGC  ACC  AAG  GTG  GAA  ATC  AAA
HZII        -    -    -    -    -    -    -    -    -    -    V    -    -    -
HZI         -    -    -    -    -    -    -    -    -    -    V    -    -    -

R
KR127VK    CGG   339

HZII       CGG
HZII        -
HZI         -
```

HUMANIZED ANTIBODY SPECIFIC FOR SURFACE ANTIGEN PRE-S1 OF HBV AND PREPARATION METHOD THEREOF

This application claims the benefit of Korean Patent Application No. 1998-49663, filed Nov. 19, 1998.

FIELD OF THE INVENTION

The present invention relates to humanized antibodies specific for HBV surface antigen pre-S1.

Particularly, this invention relates to humanized antibodies specific for HBV surface antigen pre-S1, the antibody comprising humanized heavy and light chain; to genes encoding the humanized heavy or light chain; to expression vectors containing said genes and *E. coli* transformants containing said expression vector; and to pharmaceutical composition comprising said humanized antibody, which may be administered in order to prevent HBV infection or to treat chronic hepatitis B.

BACKGROUND

HBV (Hepatitis B Virus) is responsible for chronic or acute human hepatitis that may get worse to liver cirrhosis or cancer. It is estimated that about three hundred million people are suffering from hepatitis in the world (Tiollais and Buendia, *Sci. Am.* 264:48, 1991).

There are three kinds of HBV surface proteins containing different sets of surface antigens. Particularly, these surface antigen proteins includes the Major Protein containing S antigen, the Middle Protein containing S and pre-S2 antigens, and the Large Protein containing S, pre-S2 and pre-S1 antigens (Neurath and Kent, *Adv. Virus Res.*, 34:65–142, 1988). All the surface antigen proteins can induce antibodies that neutralize HBV, and especially, antibodies against HBV pre-S antigen are associated with the elimination of the virus and the recovery from HBV infection, overcoming non-responsiveness to the S antigen (Iwarson et al., *J. Med. Virol.*, 16:89–96, 1985; Itoh et al., *Proc. Natl. Acad. Sci. USA*, 85:9174–9178, 1986; Budkowska et al., *J. Med. Virol.*, 20:111–125, 1986; Milich et al., *Proc. Natl. Acad. Sci. USA*, 82:8168–8172, 1985; Milich et al., *J. Immunol.*, 137:315–322, 1986). Unlike pre-S2 or S antigen, pre-S1 antigen is exclusively present in infectious virus particles (Heerman et al., *J. Virol.*, 52:396–402, 1984) and involved in the infection into human liver cells. Thus, it has been reported that monoclonal antibody specific for pre-S1 antigen may efficiently neutralize HBV (Neurath et al., *Cell*, 46:429, 1986; Pontisso et al., *Virology*, 173:533, 1989; Neurath et al., *Vaccine*, 7:234, 1989), and the monoclonal antibody is considered to be useful in the prevention of HBV infection and the treatment of chronic hepatitis B.

So far hepatitis B immunoglobulin has been employed as a preventive for HBV infection, which may protect, for example, a newborn baby from a HBV-positive mother, medical personnel exposed to HBV, and liver transplant patient with chronic HBV-related liver disease (Beasley et al., *Lancet*, 2:1099, 1983; Todo et al., *Hepatology*, 13:619, 1991). However, hepatitis B immunoglobulin has some shortcomings such as its limited availability, low specific activity and its possible contamination with infectious agents. Furthermore, it is another disadvantage of hepatitis B immunoglobulin that blood plasma should be continuously supplied.

As an alternative for the hepatitis B immunoglobulin, mouse monoclonal antibodies against HBV surface antigens have been developed. Although the mouse monoclonal antibodies show high affinity for the antigen and can be prepared on a large scale, they induce human anti-mouse antibody response in patients (Shawler et al., *J. Immunol.*, 135:1530, 1985). There were attempts to prepare human monoclonal antibodies, but few of these antibodies showed a high level of affinity.

Instead, humanized antibodies have been developed. Humanized antibody has a high level of affinity and specificity similar to mouse antibodies, whereas its immunogenicity is minimized. Humanized antibody is a hybrid antibody in which CDRs (Complementarity Determining Regions) of a mouse antibody is grafted to a human antibody by genetic engineering technique. It can be easily prepared on a large scale, and hardly elicits immune responses in humans since most of the DNA sequences encoding the humanized antibodies are derived from a human DNA sequence (Riechman et al., *Nature*, 332:323, 1988; Nakatani et al., *Protein Engineering*, 7:435, 1994).

To overcome the aforementioned and other disadvantages of mouse or human HBV immunoglobulin, we, the inventors of the present invention, have attempted to prepare humanized antibodies which can be used to prevent HBV infection and to treat chronic hepatitis B. Prior to this invention, we prepared a mouse monoclonal antibody KR127 against HBV surface antigen pre-S1. Additionally, we isolated the genes encoding the heavy and light chain variable regions of KR127 antibody and determined the sequences of the genes (Korea Patent Application No. 1997-30696). The present invention is performed by selecting human immunoglobulin genes homologous to the sequences of KR127 antibody light chain and heavy chain variable regions; constructing the humanized antibody genes; inserting the genes into expression vectors; introducing the vectors into host cells; obtaining humanized antibodies from the culture of the transformed cells; and confirming that the humanized antibodies have high affinity to HBV pre-S1 antigen, similar to the mouse monoclonal antibody KR127.

SUMMARY OF THE INVENTION

It is an object of this invention to provide humanized antibodies specific for CDRs of mouse HBV surface antigen pre-S1, having high affinity to the antigen and reduced immunogenicity in human.

In accordance with the present invention, the foregoing objects and advantages are readily obtained.

The present invention provides humanized antibodies specific for HBV surface antigen pre-S1, comprising humanized heavy and light chains.

This invention also provides genes encoding the variable regions of said humanized heavy or light chain.

In addition, this invention provides expression vectors containing said genes and *E. coli* transformants containing said expression vectors.

This invention further provides pharmaceutical compositions comprising said humanized antibody, which may be administered in order to prevent HBV infection or to treat chronic hepatitis B.

Further features of the present invention will appear hereinafter.

BRIEF DESCRIPTION OF THE DRAWINGS

FIG. 1*a* and FIG. 1*b* comparatively depict the amino acid and nucleotide sequences of $V_H$ regions (for Variable regions of Heavy chains) in a mouse monoclonal antibody KR127 and in two humanized antibodies of this invention, FIG. 2a schematically depicts a process for preparing HKR127HC(I) gene encoding the heavy chain of a humanized antibody of this invention, FIG. 2b schematically depicts a process for preparing HKR127HC(III) gene encoding the heavy chain of a humanized antibody of this invention, FIG. 3a and FIG. 3b comparatively depict the amino acid and nucleotide sequences of $V_L$ regions (for Variable regions in Light chain) in a mouse monoclonal antibody KR127 and in a humanized antibody of this invention.

DETAILED DESCRIPTION OF PREFERRED EMBODIMENTS

Figure 2A:
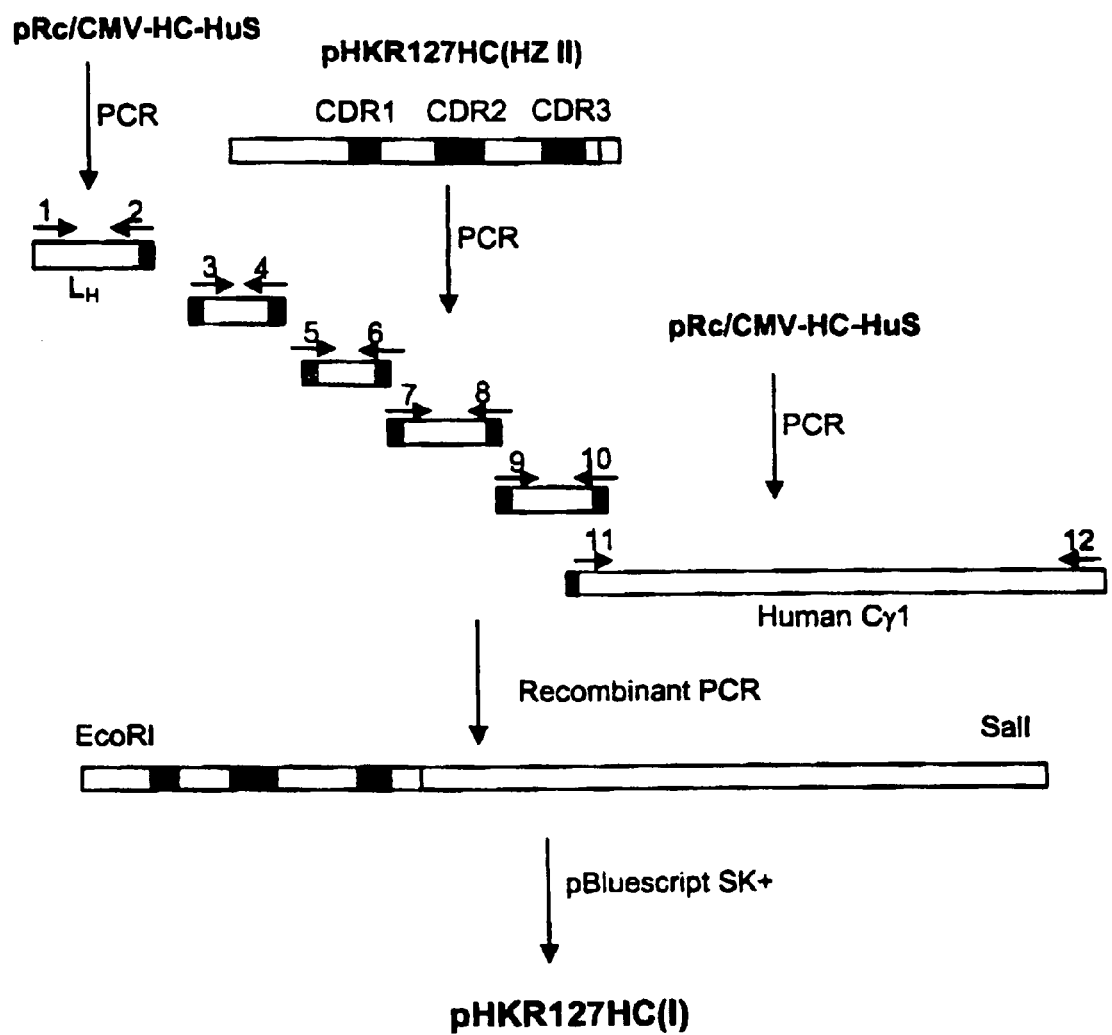

Hereinafter, the present invention is described in detail.

This invention provides humanized antibodies specific for HBV surface antigen pre-S1, comprising humanized heavy and humanized light chains.

This invention also provides genes encoding the variable regions of said humanized heavy or light chain.

Said humanized heavy chain contains variable region which is derived from the $V_H$ region of mouse KR127 antibody. The $V_H$ region of mouse KR127 antibody is described by SEQ ID NO: 19, and the $V_H$ region of the humanized antibody of this invention can be prepared by grafting the CDRs of mouse KR127 $V_H$ region to homologous human immunoglobulin $V_H$ region.

And said humanized light chain contains variable region which is derived from the $V_L$ region of mouse KR127 antibody. The $V_L$ region of mouse KR127 antibody is described by SEQ ID NO: 22, and the $V_L$ region of the humanized antibody of this invention can be prepared by grafting the CDRs of mouse KR127 $V_L$ region to homologous human immunoglobulin $V_L$ region.

In preferred embodiments, we screened human immunoglobulin that show the highest similarities of amino acid sequence to the heavy or light chain of the mouse monoclonal antibody KR127. In result, human immunoglobulin germ line genes DP7 and DPK12 were screened from GenBank database. DP7 shows the highest homology to the $V_H$ region of mouse antibody KR127, while DPK12 is most similar to the $V_L$ region of KR127.

The humanized antibodies of this invention can be produced from recombinant genes encoding humanized $V_H$ region or $V_L$ region. These genes are constructed by substituting CDRs of mouse KR127 for those of the human DP7 or DPK12 antibody. In constructing these genes, most of the amino acid residues corresponding to the humanized CDRs are derived from the CDRs of mouse antibody KR127. However, some mouse-derived CDRs residues are replaced by human counterparts, since their corresponding amino acid residues are expected not to be involved in the antigen binding (see FIG. 1). In the same way, some human-derived amino acid residues for the non-CDR framework regions (FR) of variable region are replaced with mouse counterparts, since it is expected that these FR residues may affect the conformation of CDRs.

Particularly, HKR127HCv(HZII) gene encoding a humanized $V_H$ region was prepared by grafting the partial CDR1, 2, 3 and a FR residue (at position 72) of mouse KR127 heavy chain to the human DP7 gene (see FIG. 1).

However, antibody expressed from HKR127HCv(HZII) gene did not show any significant level of binding capacity to corresponding antigen. To improve the HKR127HCv (HZII) gene, we also prepared HKR127HCv(HZI) gene and HKR127HCv(HZIII) gene which contain more mouse-derived codons than HKR127HCv(HZII) gene (see FIG. 1).

HKR127HCv(HZI) contains CDR1, partial CDR2, and CDR3, and 11 FR residues of mouse KR127 $V_H$, while HKR127HCv(HZIII) contains the same mouse CDR codons and 2 mouse FR residues (see FIG. 1).

To construct HKR127HC(I) gene encoding a full-length heavy chain of the humanized antibody of this invention, PCRs were conducted, in which template for amplification is either the HKR127HCv(HZII) gene or pRC/CMV-HC-HuS (KCTC 0229BP) containing the heavy chain leader sequence and the constant region sequence of human immunoglobulin heavy chain γ1.

Six pairs of oligonucleotides (SEQ ID NO: 1 and 2; 3 and 4; 5 and 6; 7 and 8; 9 and 10; and 11 and 12) were used as PCR primers (see FIG. 2a).

The first five PCR products were brought to annealing reaction. Then, the DNA fragment containing the five PCR products was employed as a template of recombinant PCR wherein two primers described by SEQ ID NO: 1 and 10 were used. Another recombinant PCR was conducted to link the amplified 431-bp DNA fragment to DNA fragment which was obtained by PCR using two primers (described by SEQ ID NO: 11 and 12). The recombinant PCR employed two primers described by SEQ ID NO: 1 and 12. The final 1431-bp PCR product, HKR127HC(I), encoding the heavy chain of a humanized antibody (HZKR127I) was introduced into pBluescript SK(+) vector (Clontech), and the resulting vector was designated pHKR127HC(I).

The primers are described in SEQ ID NO: 1 to 12 in SEQUENCE LISTING, and particularly, primer described by SEQ ID NO: 1 contains EcoRI sequence at the 5' end, while primer described by SEQ ID NO: 12 does SalI sequence at the 3' end.

The variable region in the HKR127HC(I) gene contains 11 mouse-derived FR residues at positions 12, 28, 30, 48, 67, 68, 70, 72, 74, 79 and 95 (see FIG. 1). The heavy chain variable region has 87 FR residues, and the unmodified FR residues is 76. Thus, the amino acid sequence of the heavy chain variable FR of the HKR127HC(I) gene is 87% homologous to that of human DP7 gene.

To more humanize the HZKR127(I), HZKR127(III) gene was constructed, which contains HKR127HCv(HZIII) gene with 2 mouse-derived FR residues at position 72 and 74 (see FIG. 1).

Figure 2B:
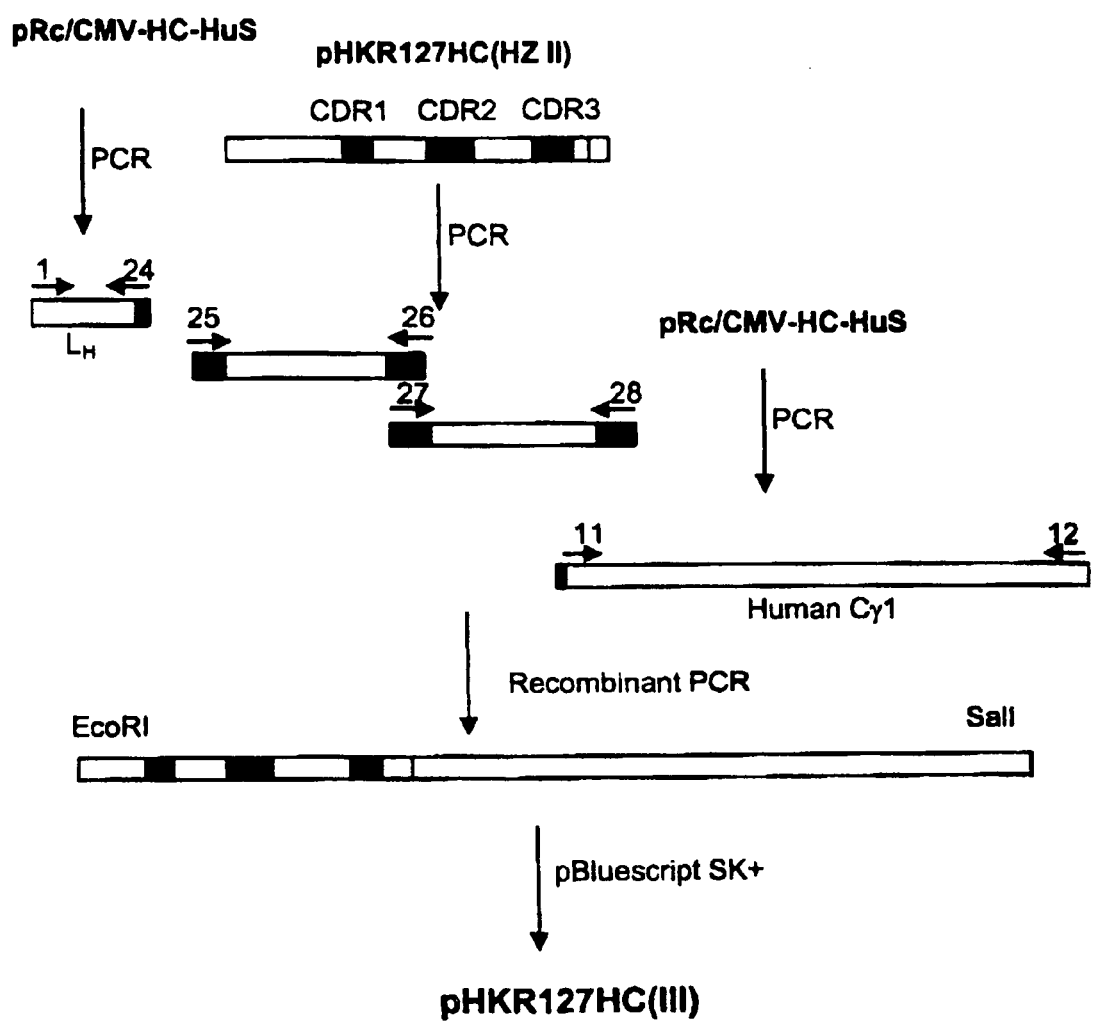

To construct HKR127HC(III) gene encoding a full-length heavy chain of the humanized antibody of this invention, PCRs were conducted, in which template for amplification is either the HKR127HCv(HZII) gene or pRC/CMV-HC-HuS (KCTC 0229BP) containing the heavy chain leader sequence and the constant region sequence of human immunoglobulin heavy chain γ1 (see FIG. 2b).

Four pairs of oligonucleotides (SEQ ID NO: 1 and 24; 25 and 26; 27 and 28; and 11 and 12) were used as PCR primers (see FIG. 2b). The first three PCR products were brought to annealing reaction. Then, the DNA fragment containing the three PCR products was employed as a template of recombinant PCR wherein two primers described by SEQ ID NO: 1 and 28 were used. Another recombinant PCR was conducted to link the amplified 431-bp DNA fragment to DNA fragment which was obtained by PCR using two primers (described by SEQ ID NO: 11 and 12). The recombinant PCR employed two primers described by SEQ ID NO: 1 and 12.

The final 1431-bp PCR product, HKR127HC(III), encoding the heavy chain of a humanized antibody (HZKR127III) was introduced into pBluescript SK(+) vector (Clontech), and the resulting vector was designated pHKR127HC(III).

In a further embodiment, HKR127KCv(HZII) gene encoding a humanized $V_L$ region was prepared by grafting the CDR1, CDR3 and partial CDR2 of mouse KR127 light chain to the human DPK12 gene (see FIG. 3).

However, antibody expressed by using the HKR127KCv (HZII) gene did not show any significant level of binding capacity to corresponding antigen. To improve the binding capacity of HKR127KCv(HZII), we also prepared HKR127KCv(HZI) gene which contains more mouse-derived amino acid residues (see FIG. 3) than HKR127HKCv (HZII) (see FIG. 3).

To construct HKR127KC(I) gene encoding a full-length light chain of the humanized antibody of this invention, PCRs were conducted, in which template for amplification is either the HKR127KCv(HZII) gene or pKC-dfhr-HuS (KCTC 0230BP) containing the light chain leader sequence and the constant region sequence of human immunoglobulin light chain κ.

Figure 4:
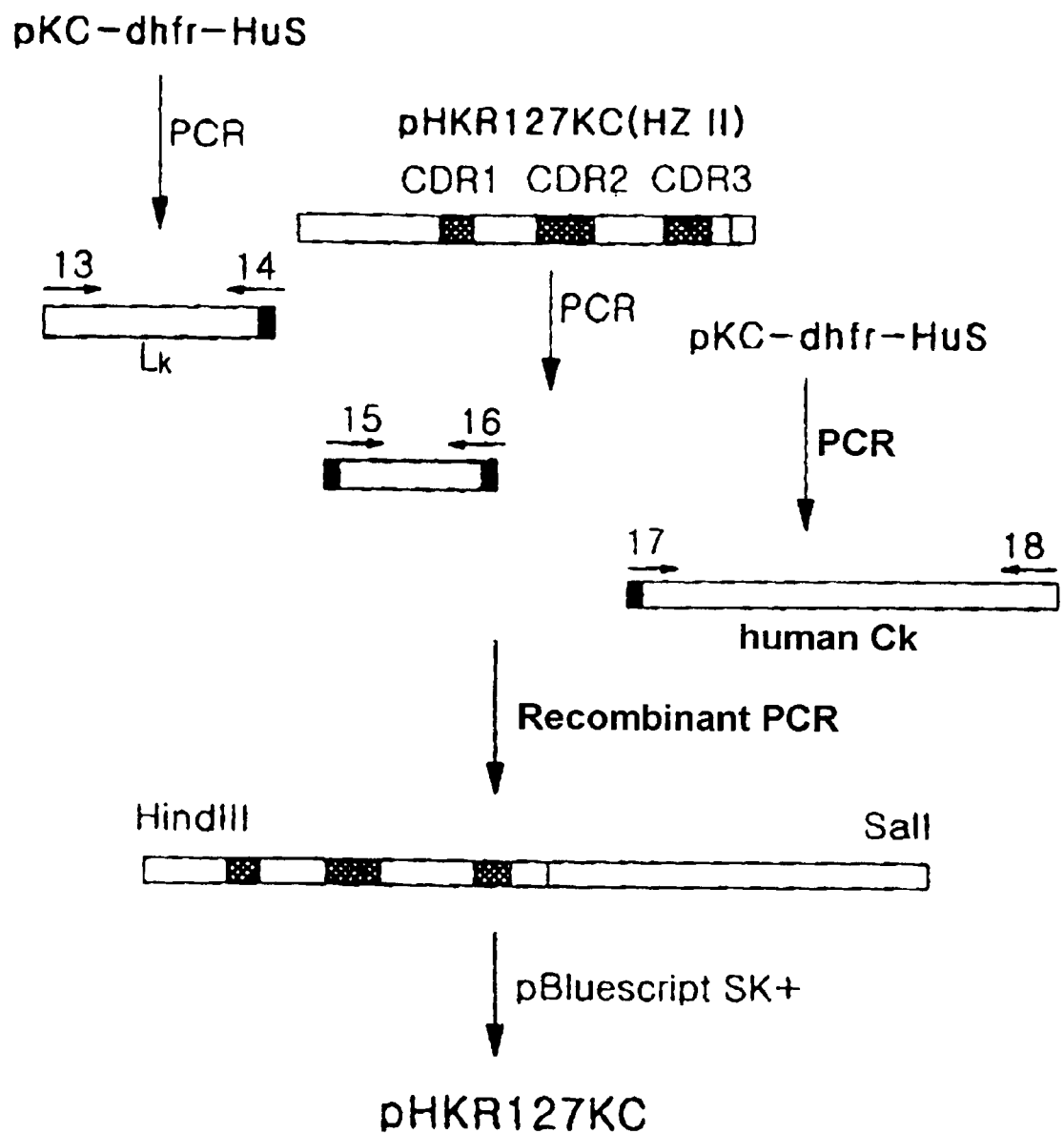
FIG. 4 schematically depicts a process for preparing HKR127KC(I) gene encoding a humanized antibody of this invention.

Three pairs of oligonucleotides (SEQ ID NO: 13 and 14; 15 and 16; and 17 and 18) were used as PCR primers (see FIG. 4).

The first two PCR products were brought to annealing reaction. Then, the DNA fragment containing the two PCR products was employed as a template of recombinant PCR wherein two primers described by SEQ ID NO: 13 and 16 were used. Another recombinant PCR was conducted to link the amplified 360-bp DNA fragment to DNA fragment which was obtained by PCR using two primers (described by SEQ ID NO: 17 and 18). The recombinant PCR employed two primers which are described by SEQ ID NO: 13 and 18. The final 739-bp PCR product, HKR127KC(I), encoding the light chain of a humanized antibody (HZKR127I) was introduced into pBluescript SK(+) vector (Clontech), and the resulting vector was designated pHKR127KC(I).

The primers are described in SEQ ID NO: 13 to 18 in SEQUENCE LISTING, and particularly, primer described by SEQ ID NO: 13 contains HindIII sequence at the 5' end, while primer described by SEQ ID NO: 18 does SalI sequence at the 3' end.

The variable region FR of the HKR127KC gene contains 5 mouse KR127-derived codons (see FIG. 3). The light chain has 83 FR residues, and the unmodified FR residues is 78. Thus, the amino acid sequence of the light chain variable FR of the HKR127KC gene is 94% identical to that of human DP7 gene.

In addition, this invention provides expression vectors containing genes encoding the humanized $V_H$ or $V_L$ region and provides E. coli transformants containing said expression vector.

Figure 5A:
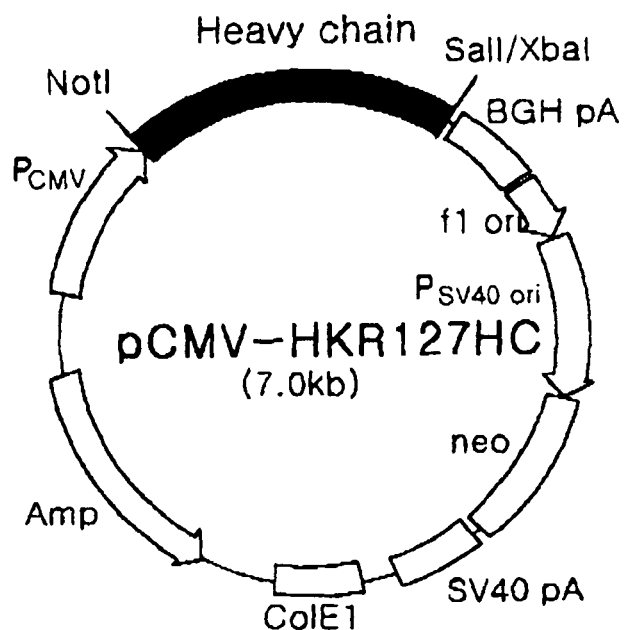
FIG. 5a depicts an expression vector pCMV-HKR127HC containing a gene for heavy chain of the humanized antibody.
Figure 5B:
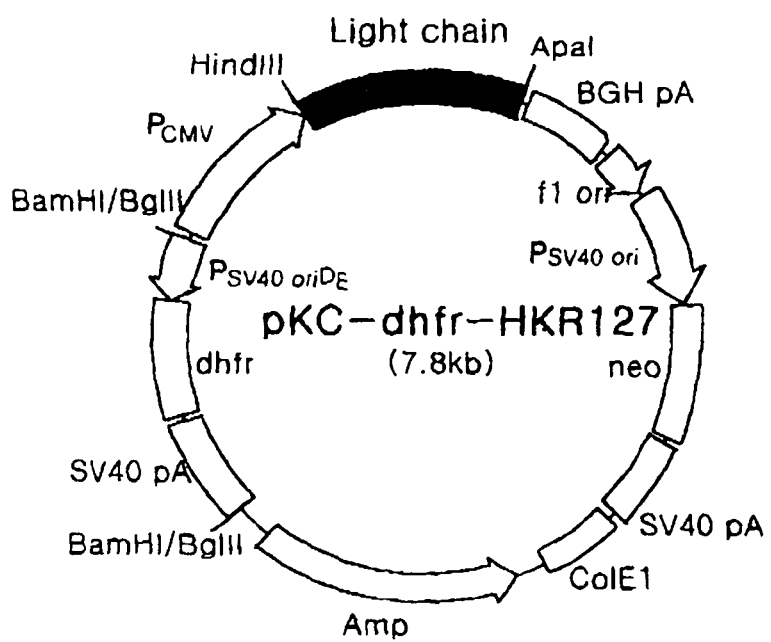
FIG. 5b depicts an expression vector pKC-dhfr-HKR127 containing a gene for light chain of the humanized antibody.
Figure 5C:
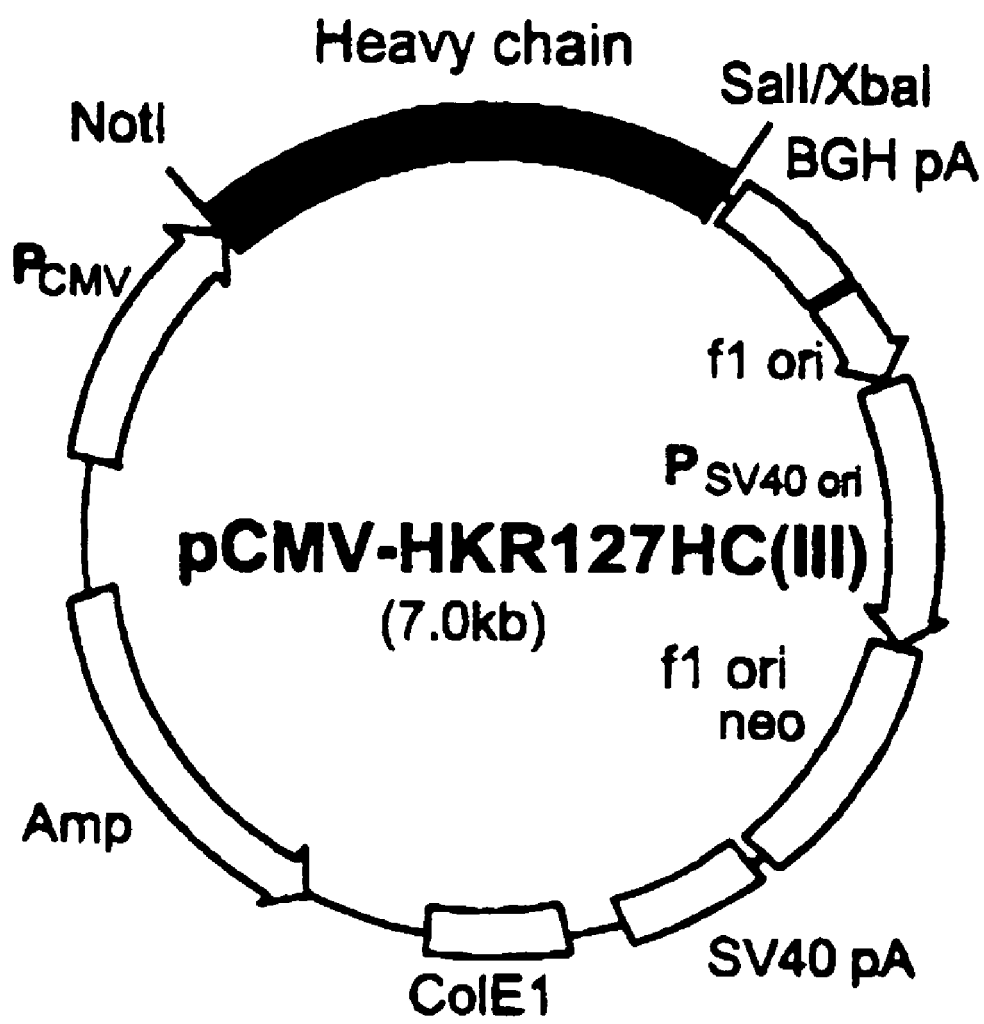
FIG. 5c depicts an expression vector pCMV-HKR127HC (III) containing a gene for heavy chain of the humanized antibody, FIG. 6a comparatively shows the binding affinities of a humanized antibody (HZKR127I) and a mouse monoclonal antibody (KR127), and FIG. 6b comparatively shows the binding affinities of a humanized antibody (HZKR127III) and a humanized antibody (HZKR127I).

In other preferred embodiments, expression vectors are prepared, which contain the gene encoding the heavy or light chain of humanized antibody (see FIGS. 5a, 5b or 5c).

Particularly, two kinds of DNA fragment corresponding to humanized heavy chain was respectively obtained from the plasmids pHKR127HC(I) and pHKR127HC(III) by treatment of restriction enzymes, and then inserted into pRc/CMV (Invitrogen) to give expression vector pCMV-HKR127HC (see FIG. 5a) and pCMV-HKR127(III)HC (see FIG. 5c), respectively.

In addition, DNA fragment encoding the humanized light chain was isolated from the pHKR127KC vector, and then introduced into pCMV-dfhr (KCTC 8671P) to construct expression vector pKC-dhfr-HKR127 (see FIG. 5b).

E. coli strain DH5α was transformed with the expression vector pCMV-HKR127HC, pCMV-HKR127(III)HC or pKC-dhfr-HKR127. The resulting E. coli transformants containing pCMV-HKR127HC or pKC-dhfr-HKR127 were deposited in KCTC (Korean Collection for Type Culture) (Accession Number: KCTC 0531BP and KCTC 0529BP, respectively) on Oct. 12, 1998. The E. coli transformant containing pCMV-HKR127(III)HC was deposited in KCTC (Accession Number: KCTC 0691BP, respectively) on Nov. 15, 1999.

In another preferred embodiment, humanized antibodies specific for HBV surface antigen pre-S1 were expressed in animal cells and obtained from culture media of the cells. COS7 cells were transiently cotransfected with the expression vectors pCMV-HKR127HC and pKC-dhfr-HKR127, and the resulting transfected cells was cultured and the culture supernatant was used to characterize a humanized antibody HZKR127I of the present invention. COS7 cells were also cotransfected with the expression vectors pCMV-HKR127(III)HC and pKC-dhfr-HKR127, and the culture supernatant of transfected cells was used to characterize a humanized antibody HZKR127III.

This invention further provides pharmaceutical compositions containing said humanized antibody.

Figure 6A:
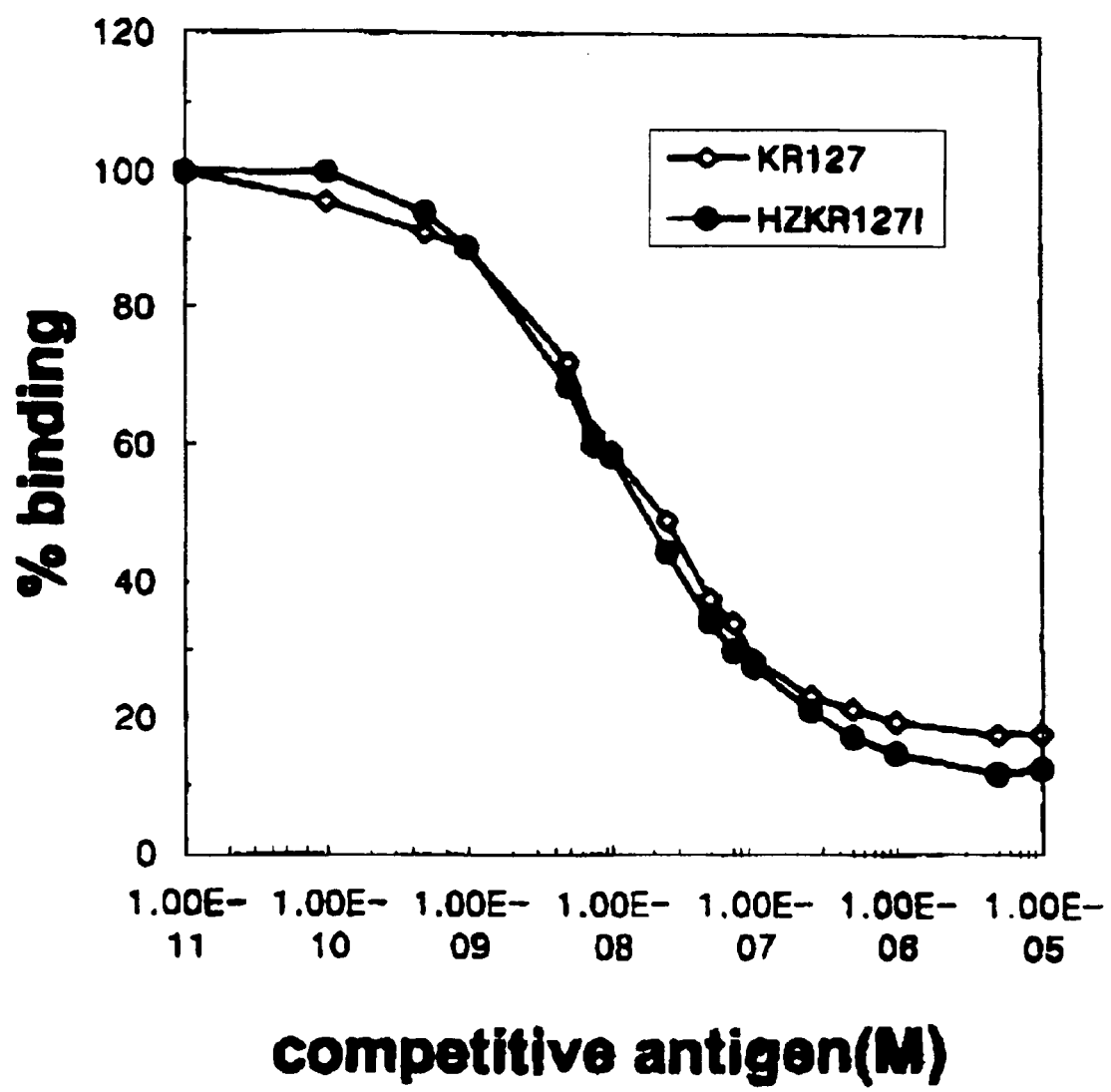
Figure 6B:
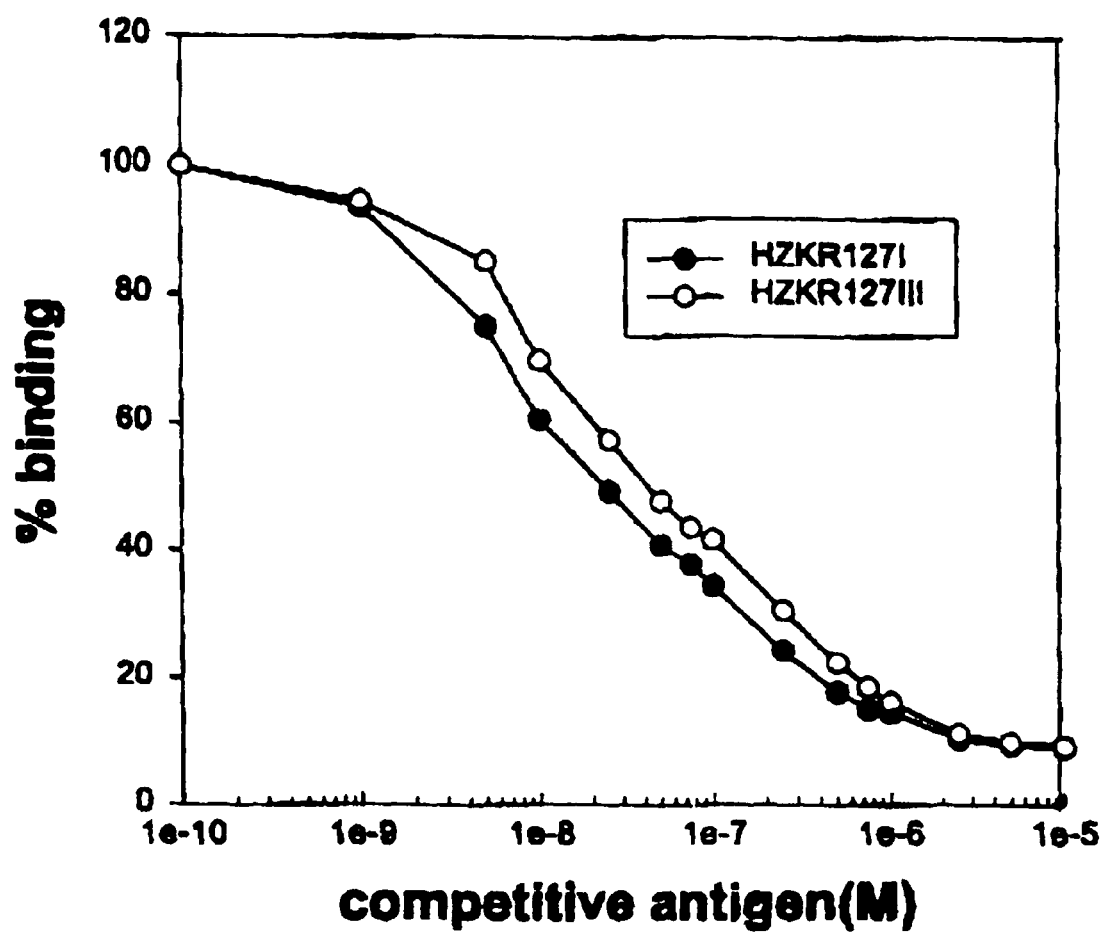

According to still other preferred embodiments, it was verified that HZKR127I and HZKR127III humanized antibodies of the present invention, showed almost same antigen-binding affinity when compared with mouse monoclonal antibody KR127 (see Table 1, 2 and FIGS. 6a, 6b).

The composition includes a therapeutically effective amounts of the humanized antibody against HBV antigen pre-S1, with/without a pharmaceutically acceptable delivery vehicle. Moreover, the compositions may include other anti-hepatitis drug(s), such as anti-S monoclonal antibody or lamivudin.

The humanized antibody against HBV antigen pre-S1 may be formulated with a pharmaceutical vehicle or diluent for intravenous, subcutaneous, intramuscular administration. The pharmaceutical composition can be formulated in a classical manner using solid or liquid vehicles, diluents and additives appropriate to the desired mode of administration.

The humanized antibody of this invention may be administered in a dosage range of about 1~10 mg/kg, preferably 3~5 mg/kg, and may be administered once a week.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Gene Encoding Humanized Heavy Chain

In order to construct the humanized heavy chain variable region gene, first, we selected a human immunoglobulin heavy chain gene that shows the highest homology of amino acid sequence to the heavy chain variable region of the mouse monoclonal antibody KR127. As the result, a human immunoglobulin germ line gene DP7 was selected from GenBank database. Then, we constructed a humanized $V_H$ region gene HKR127HCv(HZII) by DNA recombination techniques, which was based upon the comparison of the mouse KR127 $V_H$ region with the human DP7 $V_H$ region. Since the humanized heavy chain did not show significant antigen binding activity, we prepared HKR127HCv(HZI) gene encoding another $V_H$ region in order to improve the HKR127HCv(HZII) gene (see FIG. 1).

Particularly, the HKR127HCv(HZII) gene was constructed by grafting the $V_H$ region of human DP7 gene with the partial CDR1, 2, and 3 and one FR residue at position 72 of mouse KR127 $V_H$ region. It was assumed that the human CDRs and FR amino acid residues affected the antigen-binding affinity of the antibody.

Therefore, HKR127HCv(HZI) gene was constructed by PCR employing HKR127HCv(HZII) gene as a template.

On the other hand, a vector pRc/CMV-HC-HuS (Accession Number: KCTC 0229BP) was used to synthesize DNA sequence encoding human $C_H$ region as well as heavy chain leader sequence, which is required in proper secretion of the heavy chain.

Finally, HKR127HC(I) gene encoding a humanized heavy chain was constructed by recombinant PCR for the annealing of the heavy chain leader sequence, HKR127HCv(HZI) gene, and the human $C_H$ gene (see FIG. 2a).

The primers in these PCRs are synthetic oligonucleotides described by SEQ ID NO: 1 to 12. PCR was performed by using Taq DNA polymerase, and its thermocycle was repeated 30 times, consisting of 1 minute at 94° C., 1 minute at 55° C., and then 1 minute at 72° C. Five pairs of oligonucleotides (SEQ ID NO: 1 and 2; 3 and 4; 5 and 6; 7 and 8; and 9 and 10) were used as PCR primers, and the five PCR products (113 bp; 96 bp; 120 bp; 78 bp; and 87 bp, respectively) were brought to annealing reaction. Then, the DNA fragments containing the five PCR products were employed as template of the recombinant PCR wherein primers described by SEQ ID NO: 1 and 10 were used. Another recombinant PCR was conducted to link the amplified 431-bp DNA fragment to 1015-bp DNA fragment which was obtained by PCR using two primers (described by SEQ ID NO: 11 and 12). The recombinant PCR employed two primers described by SEQ ID NO: 1 and 12.

The final PCR product (HKR127HC(I), about 1431-bp) encoding a recombinant heavy chain of humanized antibody was introduced into the EcoRI-SalI site of pBluescript SK(+) vector (Clontech), and the resulting vector was designated pHKR127HC(I). The DNA sequence of the inserted gene was determined by dideoxynucleotide method.

To more humanize the HKR127HC(I), another humanized heavy chain gene, HKR127(III), which has much less number of mouse FR residues, was constructed.

To construct the HKR127HC(III), HKR127HCv(HZIII) gene was constructed by PCR employing HKR127HCv (HZII) gene as a template. On the other hand, a vector pRc/CMV-HC-HuS (Accession Number: KCTC 0229BP) was used to synthesize DNA sequence encoding human $C_H$ region as well as heavy chain leader sequence, which is required in proper secretion of the heavy chain.

Finally, HKR127HC(III) gene encoding a humanized heavy chain was constructed by recombinant PCR for annealing of the heavy chain leader sequence, HKR127HCv (HZIII) gene, and the human $C_H$ gene (see FIG. 2b).

The primers in these PCRs are synthetic oligonucleotides described by SEQ ID NO: 24 to 28. PCR was performed by using Taq DNA polymerase, and its thermocycle was repeated 30 times, consisting of 1 minute at 94° C., 1 minute at 55° C., and then 1 minute at 72° C. Three pairs of oligonucleotides (SEQ ID NO: 1 and 24; 25 and 26; and 27 and 28) were used as PCR primers, and the three PCR products (179 bp; 141 bp; and 87 bp, respectively) were brought to annealing reaction. Then, the DNA fragments containing the three PCR products were employed as template of the recombinant PCR wherein primers described by SEQ ID NO: 1 and 28 were used. Another recombinant PCR was conducted to link the amplified 431-bp DNA fragment to 1015-bp DNA fragment which was obtained by PCR using two primers (described by SEQ ID NO: 11 and 12). The recombinant PCR employed two primers described by SEQ ID NO: 1 and 12.

The final PCR product (HKR127HC(III), about 1431-bp) encoding a recombinant heavy chain of humanized antibody was introduced into the EcoRI-SalI site of pBluescript SK(+) vector (Clontech), and the resulting vector was designated pHKR127HC(III). The DNA sequence of the inserted gene was determined by dideoxynucleotide method.

Example 2

Preparation of Gene Encoding Humanized Light Chain

In order to prepare humanized light chain containing variable region, we devised genes encoding the light chain. First, we selected a human κ immunoglobulin gene that shows the highest homology of amino acid sequence to the light chain of the mouse monoclonal antibody KR127. As the result, a human κ immunoglobulin gene DPK12 was selected from GenBank database. Then, we constructed HKR127KCv(HZII) gene encoding a humanized $V_L$ region by grafting CDR1, partial CDR2, and CDR3 and one FR residue at position 41 of the mouse KR127 $V_L$ region to the human DPK12 $V_L$ region. The resulting humanized $V_L$ was not functional in antigen-binding. To improve the HKR127KCv(HZII) gene, we constructed HKR127KCv (HZI) gene encoding another $V_L$ region (see FIG. 3).

The HKR127KCv(HZI) gene was constructed by grafting the $V_L$ region of human DPK12 antibody with a few FR residues and CDR1, CDR2 and CDR3 of mouse KR127 $V_L$ (see FIG. 3).

On the other hand, a vector pKC-dhfr-HuS (Accession Number: KCTC 0230BP) was used to synthesize DNA sequence encoding human $C_L$ region as well as light chain leader sequence, which is required in proper secretion of the light chain.

Finally, HKR127KC(I) gene encoding a humanized light chain was prepared by recombinant PCR for the annealing of the PCR products, light chain leader sequence, the HKR127KCv(HZI) gene, and the human $C_L$ gene (see FIG. 4).

The primers in these PCRs are synthetic oligonucleotides described by SEQ ID NO: 13 to 18. The thermocycle of these PCRs was repeated 30 times, consisting of 1 minute at 94° C., 1 minute at 55° C., and 1 minute at 72° C. Two pairs of oligonucleotides (SEQ ID NO: 13 and 14; and SEQ ID NO: 15 and 16) were used as PCR primers, and the two PCR products (101 bp and 159 bp, respectively) were brought to annealing reaction. Then, the DNA fragments containing the two PCR products was employed as a template of recombinant PCR wherein primers described by SEQ ID NO: 13 and 16 were used. Another recombinant PCR was conducted to link the amplified 248-bp DNA fragment to 515-bp DNA fragment which was obtained by PCR using two primers (described by SEQ ID NO: 17 and 18). The recombinant PCR employed two primers described by SEQ ID NO: 13 and 18.

The final PCR product (HKR127KC(I), 736-bp) encoding a recombinant light chain of humanized antibody was introduced into the HindIII-SalI site of pBluescript SK(+) vector (Clontech), and the resulting vector was designated pHKR127KC(I). The DNA sequence of the inserted gene was determined by dideoxynucleotide method.

Example 3

Construction of Expression Vector Containing the Humanized Heavy Chain Gene

The pHKR127HC(I) or pHKR127HC(III) plasmid of Example 1 was digested with SalI enzyme, and the both ends of the vector was made blunt using Klenow enzyme treatment. This DNA fragment was further digested with NotI enzyme to obtain the gene encoding humanized heavy chain.

On the other hand, pRc/CMV (Invitrogen) was cut with XbaI enzyme, and the ends of the vector was made blunt by treating with Klenow enzyme, and then digested with NotI.

The humanized heavy chain gene and the linearized vector were linked to give expression vector pCMV-HKR127HC or pCMV-HKR127(III)HC. The *E. coli* transformant containing pCMV-HKR127HC or pCMV-HKR127(III)HC was deposited in KCTC (Korean Collection for Type Culture) (Accession Number: KCTC 0531BP and KCTC 0691BP, respectively), and the expression vector pCMV-HKR127HC and pCMV-HKR127(III)HC is shown in FIGS. 5a and 5c, respectively.

Example 4

Construction of Expression Vector Containing the Humanized Light Chain Gene

The pHKR127KC vector of Example 2 was digested with HindIII and ApaI enzymes, and the resulting fragment was inserted into HindIII-ApaI site of pCMV-dhfr (Accession Number: KCTC 8671P) to give expression vector pKC-dhfr-HKR127. The *E. coli* transformant containing pKC-dhfr-HKR127 was deposited in KCTC (Korean Collection for Type Culture) (Accession Number: KCTC 0529BP), and the expression vector pKC-dhfr-HKR127 is shown in FIG. 5b.

Example 5

Expression of Humanized Antibody in COS7 Cells

COS7 cells were maintained in DMEM (Gibco) supplemented by 10% calf serum at 37° C., under 5% $CO_2$ condition. The cells were inoculated in 100 mm petri dishes, and then incubated at 37° C. overnight.

To express a humanized antibody HZKR127I, 5 µg of pCMV-HKR127HC or pKC-dhfr-HKR127 was diluted with 800 µl of OPTI MEM I (Gibco), and 50 µl of Lipofectamin (Gibco) was also diluted with 800 µl of OPTI MEM I. These mixtures in 15-ml tubes were incubated at room temperature for 15 minutes or more. In the meantime, COS7 cells were washed twice with OPTI MEM I.

OPTI MEM I (6.4 ml) was added to the DNA-Lipofectamin mixture, mixed well, and poured on the COS7 cells. After the cells were cultured in a $CO_2$ incubator for 72 hours, the medium was centrifuged, and the supernatant was concentrated by ultrafiltration kit. The concentration of antibody was determined by Sandwich ELISA using anti-human IgG and anti-human IgG-HRP (horseradish peroxidase) conjugate.

To express and obtain a humanized antibody HZKR127III, the same protocol was repeated except using pCMV-HKR127(III)HC instead of using pCMV-HKR127HC.

Example 6

Binding Activity of Humanized Antibody to HBV Surface Antigen pre-S1

We prepared HBV surface antigen pre-S1 (amino acid residue 1–56; Kim and Hong, Biotechnology Letters, 17:871–876, 1995) and 1 µg of the purified pre-S1 was coated on each well in microplates. After addition of 0, 0.25, 0.5, 1, 2, 3, 4, 5, 7.5, 10, 20, or 40 ng of the humanized antibodies prepared in Example 5, indirect ELISA was performed, in which secondary antibody was Fc-specific anti-human IgG-HRP conjugate. The binding activities of the antibodies were determined by measuring OD at 492 nm.

Purified mouse KR127 antibody was used as a control, and ELISA of KR127 antibody was conducted using Fc-specific anti-mouse IgG-HRP conjugate as a secondary antibody. The result is presented in Table 1 and 2.

TABLE 1

Binding activity of KR127 and HZKR127I to HBV surface antigen pre-S1 (OD at 492 nm)

| Antibody | Amount (ng) | | | | | | | | | | | |
|---|---|---|---|---|---|---|---|---|---|---|---|---|
| | 0 | 0.25 | 0.5 | 1 | 2 | 3 | 4 | 5 | 7.5 | 10 | 20 | 40 |
| KR127 | 0.09 | 0.12 | 0.15 | 0.20 | 0.30 | 0.36 | 0.43 | 0.54 | 0.60 | 0.80 | 1.16 | 1.64 |
| HZKR127I | 0.09 | 0.12 | 0.17 | 0.26 | 0.35 | 0.43 | 0.60 | 0.71 | 0.79 | 1.12 | 1.48 | 1.77 |

TABLE 2

Binding activity of HZKR127I and HZKR127III to HBV surface antigen pre-S1 (OD at 492 nm)

| Antibody | Amount (ng) | | | | | | | | | | | |
|---|---|---|---|---|---|---|---|---|---|---|---|---|
| | 0 | 0.25 | 0.5 | 1 | 2 | 3 | 4 | 5 | 7.5 | 10 | 20 | 40 |
| HZKR127I | 0.06 | 0.19 | 0.25 | 0.58 | 0.65 | 0.75 | 0.86 | 1.02 | 1.25 | 1.39 | 1.95 | 2.07 |
| HZKR127III | 0.06 | 0.20 | 0.37 | 0.60 | 0.87 | 1.10 | 1.24 | 1.37 | 1.65 | 1.89 | 2.04 | 2.10 |

Example 7

Antigen-Binding Affinity of Humanized Antibody to HBV Surface Antigen pre-S1

Antigen-binding affinity to HBV surface antigen pre-S1 was assayed by competitive ELISA method(Ryu et al., J. Med. Virol., 52:226, 1997).

Binding reactions between the pre-S1 antigen ($1\times10^{-7}$~$1\times10^{-12}$ M) and the humanized antibody of Example 5 (5 ng), or between the antigen ($1\times10^{-7}$~$1\times10^{-12}$ M) and control antibody KR127 (5 ng), were performed at 37° C. for 2 hours. Then the reaction mixtures were added to 96-well microplates coated with the 250 ng of antigen pre-S1.

FIG. 6a shows the affinity of two kinds of antibodies. It was confirmed that the binding affinity of the humanized antibody HZKR127I is almost same as that of the mouse antibody KR127 ($7\times10^7$ M$^{-1}$) FIG. 6b shows the affinity of HZKR127III compared with that of HZKR127I. The affinity of HZKR127III ($5\times10^7$ M$^{-1}$) was not much different from that ($7\times10^7$ M$^{-1}$) of HZKR127I.

INDUSTRIAL APPLICABILITY

As shown above, the present invention provides humanized antibody against HBV surface antigen pre-S1, which shows similar level of binding affinity when compared with mouse monoclonal antibody, whereas immunogenicity of the humanized antibody is remarkably reduced. Thus, the humanized antibody of the present invention may be useful for the prevention of HBV infection and for the treatment of hepatitis B.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

---

What is claimed is:

1. A gene encoding a humanized heavy chain which comprises a humanized heavy chain variable region having an amino acid sequence selected from the group consisting of: the amino acid sequence of SEQ ID NO: 21; and the amino acid sequence of SEQ ID NO: 21 which is modified by at least one amino acid substitution selected from the group comprising: $Lys^{12} \rightarrow Val^{12}$, $Thr^{28} \rightarrow Ala^{28}$, $Thr^{30} \rightarrow Ser^{30}$, $Met^{48} \rightarrow Ile^{48}$, $Arg^{67} \rightarrow Lys^{67}$, $Val^{68} \rightarrow Ala^{68}$, $Met^{70} \rightarrow Leu^{70}$, $Val^{79} \rightarrow Ala^{79}$, and $Tyr^{95} \rightarrow Phe^{95}$.

2. The gene of claim 1, wherein the humanized heavy chain variable region comprises an amino acid sequence of SEQ ID NO: 21.

3. An expression vector containing the gene of claim 1.

4. The expression vector of claim 3, which is designated pCMV-HKR127HC (Accession Number: KCTC 0531BP).

5. The expression vector of claim 3, which is designated pCMV-H127(III)HC (Accession Number: KCTC 0691BP).

6. A humanized antibody specific for HBV surface antigen pre-S1, containing a humanized heavy chin variable region which comprises an amino acid sequence of SEQ ID NO: 21.

7. The humanized antibody of claim 6, wherein the amino add sequence of the humanized heavy chain variable region is modified from SEQ ID NO: 21 by at least one amino acid substitution selected from the group comprising:

| | | |
|---|---|---|
| $Lys^{12} \rightarrow Val^{12}$, | $Thr^{28} \rightarrow Ala^{28}$, | $Thr^{30} \rightarrow Ser^{30}$, |
| $Met^{48} \rightarrow Ile^{48}$, | $Arg^{67} \rightarrow Lys^{67}$, | $Val^{58} \rightarrow Ala^{68}$, |
| $Met^{70} \rightarrow Leu^{70}$, | $Val^{79} \rightarrow Ala^{79}$, | and $Tyr^{95} \rightarrow Phe^{95}$. |

8. A composition containing a humanized antibody specific for HBV surface ant pre-S1, wherein the humanized antibody comprises:

(a) a humanized heavy chain variable region which comprises an amino acid sequence of SEQ ID NO: 21; or (b) a humanized heavy chain variable region which comprises an amino acid sequence of SEQ ID NO: 21 which is modified by at least one amino acid substitution selected from the group comprising: $Lys^{12} \rightarrow Val^{12}$, $Thr^{28} \rightarrow Ala^{28}$, $Thr^{30} \rightarrow Ser^{30}$, $Met^{48} \rightarrow Ile^{48}$, $Arg^{67} \rightarrow Lys^{67}$, $Val^{68} \rightarrow Ala^{68}$, $Met^{70} \rightarrow Leu^{70}$, $Val^{79} \rightarrow Ala^{79}$, and $Tyr^{95} \rightarrow Phe^{95}$.

* * * * *

SEQUENCE LISTING

```
<160> NUMBER OF SEQ ID NOS: 38

<210> SEQ ID NO 1
<211> LENGTH: 26
<212> TYPE: DNA
<213> ORGANISM: Artificial Sequence
<220> FEATURE:
<223> OTHER INFORMATION: Synthetic oligonucleotide primer 1

<400> SEQUENCE: 1
gagaattcac attcacgatg tacttg                                          26

<210> SEQ ID NO 2
<211> LENGTH: 27
<212> TYPE: DNA
<213> ORGANISM: Artificial Sequence
<220> FEATURE:
<223> OTHER INFORMATION: Synthetic oligonucleotide primer 2

<400> SEQUENCE: 2
ggccccaggc ttcaccactt cagctcc                                         27

<210> SEQ ID NO 3
<211> LENGTH: 18
<212> TYPE: DNA
<213> ORGANISM: Artificial Sequence
<220> FEATURE:
<223> OTHER INFORMATION: Synthetic oligonucleotide primer 3

<400> SEQUENCE: 3
```

-continued

```
gtgaagcctg gggcctca                                            18

<210> SEQ ID NO 4
<211> LENGTH: 27
<212> TYPE: DNA
<213> ORGANISM: Artificial Sequence
<220> FEATURE:
<223> OTHER INFORMATION: Synthetic oligonucleotide primer 4

<400> SEQUENCE: 4
agaactactg aatgcgtagc cagaagc                                  27

<210> SEQ ID NO 5
<211> LENGTH: 27
<212> TYPE: DNA
<213> ORGANISM: Artificial Sequence
<220> FEATURE:
<223> OTHER INFORMATION: Synthetic oligonucleotide primer 5

<400> SEQUENCE: 5
gcattcagta gttcttggat gaactgg                                  27

<210> SEQ ID NO 6
<211> LENGTH: 27
<212> TYPE: DNA
<213> ORGANISM: Artificial Sequence
<220> FEATURE:
<223> OTHER INFORMATION: Synthetic oligonucleotide primer 6

<400> SEQUENCE: 6
aatccgtcca atccactcaa gaccctg                                  27

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide primer 7

<400> SEQUENCE: 7
tggattggac ggatttatcc t                                        21

<210> SEQ ID NO 8
<211> LENGTH: 39
<212> TYPE: DNA
<213> ORGANISM: Artificial Sequence
<220> FEATURE:
<223> OTHER INFORMATION: Synthetic oligonucleotide primer 8

<400> SEQUENCE: 8
ggatttgtct gcagtcagtg tggccttgcc ctggaactt                     39

<210> SEQ ID NO 9
<211> LENGTH: 39
<212> TYPE: DNA
<213> ORGANISM: Artificial Sequence
<220> FEATURE:
<223> OTHER INFORMATION: Synthetic oligonucleotide primer 9

<400> SEQUENCE: 9
actgcagaca aatccacgag cacagcctac atggagctc                     39

<210> SEQ ID NO 10
<211> LENGTH: 33
<212> TYPE: DNA
```

```
<213> ORGANISM: Artificial Sequence
<220> FEATURE:
<223> OTHER INFORMATION: Synthetic oligonucleotide primer 10

<400> SEQUENCE: 10
gtcgtactct cttgcacaga aatagaccgc cgt                              33

<210> SEQ ID NO 11
<211> LENGTH: 33
<212> TYPE: DNA
<213> ORGANISM: Artificial Sequence
<220> FEATURE:
<223> OTHER INFORMATION: Synthetic oligonucleotide primer 11

<400> SEQUENCE: 11
gcaagagagt acgacgaggc ttactggggc caa                              33

<210> SEQ ID NO 12
<211> LENGTH: 26
<212> TYPE: DNA
<213> ORGANISM: Artificial Sequence
<220> FEATURE:
<223> OTHER INFORMATION: Synthetic oligonucleotide primer 12

<400> SEQUENCE: 12
cggtcgactc atttacccgg agacag                                     26

<210> SEQ ID NO 13
<211> LENGTH: 26
<212> TYPE: DNA
<213> ORGANISM: Artificial Sequence
<220> FEATURE:
<223> OTHER INFORMATION: Synthetic oligonucleotide primer 13

<400> SEQUENCE: 13
caaagcttgg aagcaagatg gattca                                     26

<210> SEQ ID NO 14
<211> LENGTH: 36
<212> TYPE: DNA
<213> ORGANISM: Artificial Sequence
<220> FEATURE:
<223> OTHER INFORMATION: Synthetic oligonucleotide primer 14

<400> SEQUENCE: 14
tggagtttgg gtcatcaaga tatccccaca ggtacc                          36

<210> SEQ ID NO 15
<211> LENGTH: 48
<212> TYPE: DNA
<213> ORGANISM: Artificial Sequence
<220> FEATURE:
<223> OTHER INFORMATION: Synthetic oligonucleotide primer 15

<400> SEQUENCE: 15
atgacccaaa ctccactttc tttgtcggtt accctggac aaccagcc              48

<210> SEQ ID NO 16
<211> LENGTH: 39
<212> TYPE: DNA
<213> ORGANISM: Artificial Sequence
<220> FEATURE:
<223> OTHER INFORMATION: Synthetic oligonucleotide primer 16

<400> SEQUENCE: 16
caccagatag attaggcgct ttggagactg gcctggctt                       39
```

<210> SEQ ID NO 17
<211> LENGTH: 39
<212> TYPE: DNA
<213> ORGANISM: Artificial Sequence
<220> FEATURE:
<223> OTHER INFORMATION: Synthetic oligonucleotide primer 17

<400> SEQUENCE: 17
ctaatctatc tggtgtctaa actggactct ggagtccct                    39

<210> SEQ ID NO 18
<211> LENGTH: 17
<212> TYPE: DNA
<213> ORGANISM: Artificial Sequence
<220> FEATURE:
<223> OTHER INFORMATION: Synthetic oligonucleotide primer 18

<400> SEQUENCE: 18
gaagtcgacc taacact                                            17

<210> SEQ ID NO 19
<211> LENGTH: 115
<212> TYPE: PRT
<213> ORGANISM: Artificial Sequence
<220> FEATURE:
<223> OTHER INFORMATION: Variable region of heavy chain in mouse KR127
      antibody

<400> SEQUENCE: 19

Gln Val Gln Leu Gln Gln Ser Gly Pro Glu Leu Val Lys Pro Gly Ala
 1               5                  10                  15

Ser Val Lys Ile Ser Cys Lys Ala Ser Gly Tyr Ala Phe Ser Ser Ser
                20                  25                  30

Trp Met Asn Trp Val Lys Gln Arg Pro Gly Gln Gly Leu Glu Trp Ile
            35                  40                  45

Gly Arg Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Val Asp Ser Ala Val Tyr Phe Cys
                85                  90                  95

Ala Arg Glu Tyr Asp Glu Ala Tyr Trp Gly Gln Gly Thr Leu Val Thr
                100                 105                 110

Val Ser Ala
        115

<210> SEQ ID NO 20
<211> LENGTH: 115
<212> TYPE: PRT
<213> ORGANISM: Artificial Sequence
<220> FEATURE:
<223> OTHER INFORMATION: Variable region of humanized heavy chain
      HKR127HC(HZI)

<400> SEQUENCE: 20

Gln Val Gln Leu Val Gln Ser Gly Ala Glu Val Val Lys Pro Gly Ala
 1               5                  10                  15

Ser Val Lys Val Ser Cys Lys Ala Ser Gly Tyr Ala Phe Ser Ser Ser
                20                  25                  30

Trp Met Asn Trp Val Arg Gln Ala Pro Gly Gln Gly Leu Glu Trp Ile
            35                  40                  45

```
Gly Arg Ile Tyr Pro Gly Asp Gly Asp Thr Asn Tyr Ala Gln Lys Phe
        50                  55                  60

Gln Gly Lys Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Glu Tyr Asp Glu Ala Tyr Trp Gly Gln Gly Thr Leu Val Thr
                100                 105                 110

Val Ser Ser
        115

<210> SEQ ID NO 21
<211> LENGTH: 115
<212> TYPE: PRT
<213> ORGANISM: Artificial Sequence
<220> FEATURE:
<223> OTHER INFORMATION: Variable region of humanized heavy chain
      HKR127HC(HZIII)

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
                20                  25                  30

Trp Met Asn Trp Val Arg Gln Ala Pro Gly Gln Gly Leu Glu Trp Met
            35                  40                  45

Gly Arg Ile Tyr Pro Gly Asp Gly Asp Thr Asn Tyr Ala Gln Lys Phe
        50                  55                  60

Gln Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Tyr Asp Glu Ala Tyr Trp Gly Gln Gly Thr Leu Val Thr
                100                 105                 110

Val Ser Ser
        115

<210> SEQ ID NO 22
<211> LENGTH: 113
<212> TYPE: PRT
<213> ORGANISM: Artificial Sequence
<220> FEATURE:
<223> OTHER INFORMATION: Variable region of light chain in mouse KR127
      antibody

<400> SEQUENCE: 22

Asp Ile Leu Met Thr Gln Thr Pro Leu Ile Leu Ser Val Thr Ile Gly
1               5                   10                  15

Gln Pro Ala Ser Ile Ser Cys Lys Ser Ser Gln Ser Leu Leu Tyr Ser
                20                  25                  30

Asn Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80

Ile Arg Val Glu Ala Glu Asp Leu Gly Val Tyr Tyr Cys Val Gln Gly
                85                  90                  95
```

```
Thr His Phe Pro Gln Thr Phe Gly Gly Gly Thr Lys Leu Glu Ile Lys
            100                 105                 110
Arg

<210> SEQ ID NO 23
<211> LENGTH: 113
<212> TYPE: PRT
<213> ORGANISM: Artificial Sequence
<220> FEATURE:
<223> OTHER INFORMATION: Variable region of humanized light chain

<400> SEQUENCE: 23

Asp Ile Leu Met Thr Gln Thr Pro Leu Ser Leu Ser Val Thr Pro Gly
  1               5                  10                  15

Gln Pro Ala Ser Ile Ser Cys Lys Ser Ser Gln Ser Leu Leu Tyr Ser
             20                  25                  30

Asn Gly Lys Thr Tyr Leu Asn Trp Leu Leu Gln Lys Pro Gly Gln Ser
         35                  40                  45

Pro Lys Arg Leu Ile Tyr Leu Val Ser Lys Leu Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                 85                  90                  95

Thr His Phe Pro Gln Thr Phe Gly Gly Gly Thr Lys Val Glu Ile Lys
            100                 105                 110
Arg

<210> SEQ ID NO 24
<211> LENGTH: 27
<212> TYPE: DNA
<213> ORGANISM: Artificial Sequence
<220> FEATURE:
<223> OTHER INFORMATION: Synthetic oligonucleotide primer 24

<400> SEQUENCE: 24
gttcatccaa gaactggtga aggtgta                                        27

<210> SEQ ID NO 25
<211> LENGTH: 27
<212> TYPE: DNA
<213> ORGANISM: Artificial Sequence
<220> FEATURE:
<223> OTHER INFORMATION: Synthetic oligonucleotide primer 25

<400> SEQUENCE: 25
agttcttgga tgaactgggt gcgacga                                        27

<210> SEQ ID NO 26
<211> LENGTH: 27
<212> TYPE: DNA
<213> ORGANISM: Artificial Sequence
<220> FEATURE:
<223> OTHER INFORMATION: Synthetic oligonucleotide primer 26

<400> SEQUENCE: 26
gctcgtggat ttgtctgcag tcattgt                                        27

<210> SEQ ID NO 27
<211> LENGTH: 27
<212> TYPE: DNA
```

<210> SEQ ID NO 27
<211> LENGTH: 27 [assumed from context]
<212> TYPE: DNA
<213> ORGANISM: Artificial Sequence
<220> FEATURE:
<223> OTHER INFORMATION: Synthetic oligonucleotide primer 27

<400> SEQUENCE: 27
gacaaatcca cgagcacagt ctacatg                                           27

<210> SEQ ID NO 28
<211> LENGTH: 27
<212> TYPE: DNA
<213> ORGANISM: Artificial Sequence
<220> FEATURE:
<223> OTHER INFORMATION: Synthetic oligonucleotide primer 28

<400> SEQUENCE: 28
gtcgtactct ctcgcacagt aatacac                                           27

<210> SEQ ID NO 29
<211> LENGTH: 345
<212> TYPE: DNA
<213> ORGANISM: Artificial Sequence
<220> FEATURE:
<223> OTHER INFORMATION: KR127

<400> SEQUENCE: 29
caggtccagc tgcagcagtc tggacctgaa ctggtgaagc ctggggcctc agtgaagatt        60
tcctgcaaag cttctggcta cgcattcagt agttcttgga tgaactgggt gaagcagagg       120
cctggacagg gtcttgagtg gattggacgg atttatcctg agatggaga tactaactac        180 aatgggaagt tcaagggcaa ggccacactg actgcagaca atcctccag cacagcctac        240 atgcagctca gcagcctgac ctctgtggac tctgcggtct atttctgtgc aagagagtac       300
gacgaggctt actggggcca aggactctg gtcactgtct ctgca                        345

<210> SEQ ID NO 30
<211> LENGTH: 345
<212> TYPE: DNA
<213> ORGANISM: Artificial Sequence
<220> FEATURE:
<223> OTHER INFORMATION: HZII

<400> SEQUENCE: 30
caggtccagc tggtgcagtc tggagctgaa gtgaagaagc ctggggcctc agtgaaggtt        60
tcctgcaaag cttctggcta caccttcacc agttactgga tgaactgggt gcgacaggcc       120
cctggacagg gtcttgagtg gatgggacgg atttatcctg agatggaga tactaactac        180 gcacagaagt tccagggcag agtcacaatg actgcagaca cgtccacgag cacagtctac       240
atggagctca gcagcctgag atctgaggac acggcggtct attactgtgc aagagagtac       300
gacgaggact actggggcca aggactctg gtcactgtct cttca                        345

<210> SEQ ID NO 31
<211> LENGTH: 345
<212> TYPE: DNA
<213> ORGANISM: Artificial Sequence
<220> FEATURE:
<223> OTHER INFORMATION: HZI

<400> SEQUENCE: 31
caggtccagc tggtgcagtc tggagctgaa gtggtgaagc ctggggcctc agtgaaggtt        60
tcctgcaaag cttctggcta cgcattcagt agttcttgga tgaactgggt gcgacaggcc       120
cctggacagg gtcttgagtg gattggacgg atttatcctg agatggaga tactaactac        180

```
gcacagaagt tccagggcaa ggccacactg accgcagaca atccacgag  cacagcctac    240 atggagctga gcagcctgag atctgaggac acggcggtct atttctgtgc aagagagtac    300
gacgaggctt actggggcca aggactctg  gtcactgtct cttca                    345
```

<210> SEQ ID NO 32
<211> LENGTH: 345
<212> TYPE: DNA
<213> ORGANISM: Artificial Sequence
<220> FEATURE:
<223> OTHER INFORMATION: HZIII

<400> SEQUENCE: 32

```
caggtccagc tggtgcagtc tggagctgaa gtgaagaagc ctggggcctc agtgaaggtt    60
tcctgcaaag cttctggcta caccttcacc agttcttgga tgaactgggt gcgacaggcc    120
cctggacagg gtcttgagtg gatgggacgg atttatcctg gagatggaga tactaactac    180
gcacagaagt ccagggcag  agtcacaatg actgcagaca atccacgag  cacagtctac    240 atggagctca gcagcctgag atctgaggac acggcggtct attactgtgc aagagagtac    300
gacgaggctt actggggcca agggactctg gtcactgtct cttca                    345
```

<210> SEQ ID NO 33
<211> LENGTH: 115
<212> TYPE: PRT
<213> ORGANISM: Artificial Sequence
<220> FEATURE:
<223> OTHER INFORMATION: HZII

<400> SEQUENCE: 33

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asp Thr Asn Tyr Ala Gln Lys Phe
    50                  55                  60

Gln Gly Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Tyr Asp Glu Asp Tyr Trp Gly Gln Gly Thr Leu Val Thr
            100                 105                 110

Val Ser Ser
        115
```

<210> SEQ ID NO 34
<211> LENGTH: 339
<212> TYPE: DNA
<213> ORGANISM: Artificial Sequence
<220> FEATURE:
<223> OTHER INFORMATION: KR127

<400> SEQUENCE: 34

```
gatatcttga tgacccaaac tccacttatt ttgtcggtta ccattggaca accagcctct    60
atctcttgca agtcaagtca gagcctctta tatagtaatg gaaaaaccta tttgaattgg    120
ttattacaga ggccaggcca gtctccaaag cgcctaatct atctggtgtc taaactggac    180
```

```
tctggagtcc ctgacaggtt cactggcagt ggatcaggaa cagattttac actgaaaatc      240
atcagagtgg aggctgagga tttgggagtt tattactgcg tgcaaggtac acatttcct       300 cagacgttcg gtggaggcac caagctggaa atcaaacgg                             339
```

<210> SEQ ID NO 35
<211> LENGTH: 302
<212> TYPE: DNA
<213> ORGANISM: Artificial Sequence
<220> FEATURE:
<223> OTHER INFORMATION: DPK12

<400> SEQUENCE: 35

```
gatattgtga tgacccagac tccactctct ctgtccgtca cccctggaca gccggcctcc      60
atctcctgca gtctagtca gagcctcctg catagtgatg aaagaccta tttgtattgg        120 tacctgcaga agccaggcca gcctccacag ctcctgatct atgaagtttc caaccggttc      180
tctggagtgc agataggttt cagtggcagc gggtcaggga cagatttcac actgaaaatc     240
agccgggtgg aggctgagga tgttggggtt tattactgca tgcaaagtat acagcttcct     300
cc                                                                     302
```

<210> SEQ ID NO 36
<211> LENGTH: 339
<212> TYPE: DNA
<213> ORGANISM: Artificial Sequence
<220> FEATURE:
<223> OTHER INFORMATION: HZII

<400> SEQUENCE: 36

```
gatatcgtga tgacccaaac tccactttct ttgtcggtta cccctggaca accagcctct      60
atctcttgca agtcaagtca gagcctctta tatagtaatg gaaaaaccta tttgaattgg      120
ttattacaga agccaggcca gcctccacag ctcctaatct atctggtgtc taaacggttc      180
tctggagtcc ctgacaggtt cagtggcagt ggatcaggaa cagattttac actgaaaatc      240
agcagagtgg aggctgagga tgttggagtt tattactgcg tgcaaggtac acatttcct      300 cagacgttcg gtggaggcac caaggtggaa atcaaacgg                             339
```

<210> SEQ ID NO 37
<211> LENGTH: 113
<212> TYPE: PRT
<213> ORGANISM: Artificial Sequence
<220> FEATURE:
<223> OTHER INFORMATION: HZII

<400> SEQUENCE: 37

```
Asp Ile Val Met Thr Gln Thr Pro Leu Ser Leu Ser Val Thr Pro Gly
  1               5                  10                  15

Gln Pro Ala Ser Ile Ser Cys Lys Ser Ser Gln Ser Leu Leu Tyr Ser
             20                  25                  30

Asn Gly Lys Thr Tyr Leu Asn Trp Leu Leu Gln Lys Pro Gly Gln Pro
         35                  40                  45

Pro Gln Leu Leu Ile Tyr Leu Val Ser Lys Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                 85                  90                  95

Thr His Phe Pro Gln Thr Phe Gly Gly Gly Thr Lys Val Glu Ile Lys
```

```
                  100             105            110
Arg

<210> SEQ ID NO 38
<211> LENGTH: 294
<212> TYPE: DNA
<213> ORGANISM: Artificial Sequence
<220> FEATURE:
<223> OTHER INFORMATION: DP7

<400> SEQUENCE: 38
caggtgcagc tggtgcagtc tggggctgag gtgaagaagc ctggggcctc agtgaaggtt      60
tcctgcaagg catctggata caccttcacc agctactata tgcactgggt gcgacaggcc     120
cctggacaag ggcttgagtg gatgggaata atcaaccctc gtggtggtag cacaagctac     180
gcacagaagt tccagggcag agtcaccatg accagggaca cgtccacgag cacagtctac     240
atggagctga gcagcctgag atctgaggac acggccgtgt attactgtgc gaga           294
```